US012663487B2

(12) United States Patent
Hattersley

(10) Patent No.: US 12,663,487 B2
(45) Date of Patent: Jun. 23, 2026

(54) MAGNETIC PROBE APPARATUS

(71) Applicant: ENDOMAGNETICS LTD., Cambridge (GB)

(72) Inventor: Simon Richard Hattersley, Bickley (GB)

(73) Assignee: ENDOMAGNETICS LTD. (GB)

( * ) Notice: Subject to any disclaimer, the term of this patent is extended or adjusted under 35 U.S.C. 154(b) by 0 days.

(21) Appl. No.: 18/798,020

(22) Filed: Aug. 8, 2024

(65) Prior Publication Data

US 2024/0402269 A1 Dec. 5, 2024

Related U.S. Application Data

(63) Continuation of application No. 18/103,828, filed on Jan. 31, 2023, now Pat. No. 12,092,708, which is a
(Continued)

(51) Int. Cl.
*A61B 5/05* (2021.01)
*A61B 5/00* (2006.01)
(Continued)

(52) U.S. Cl.
CPC ............ *G01R 33/1269* (2013.01); *A61B 5/05* (2013.01); *A61B 5/065* (2013.01); *A61B 5/415* (2013.01);
(Continued)

(58) Field of Classification Search
CPC .............................. G01R 33/1269; A61B 5/05
See application file for complete search history.

(56) References Cited

U.S. PATENT DOCUMENTS 2,614,164 A    10/1952   Huston
3,445,928 A    5/1969    Beynon
(Continued)

FOREIGN PATENT DOCUMENTS

DE          29724862        3/2005
DE          102007009016    8/2008
(Continued)

OTHER PUBLICATIONS

English translation of Office Action for Japanese Patent Application No. 2008-508306, dispatched in Nov. 8, 2011, 6 pages.
(Continued)

*Primary Examiner* — Rochelle D Turchen
(74) *Attorney, Agent, or Firm* — K&L GATES LLP

(57) ABSTRACT

A system and method for locating magnetic material. In one embodiment the system includes a magnetic probe; a power module in electrical communication with the magnetic probe to supply current to the magnetic probe; a sense module in electrical communication with the magnetic probe to receive signals from the magnetic probe; and a computer in electrical communication with the power module and the sense module. The computer generates a waveform that controls the supply of current from the power module and receives a signal from the sense module that indicates the presence of magnetic material. The magnetic probe is constructed from a material having a coefficient of thermal expansion of substantially $10^{-6}/°$ C. or less and a Young's modulus of substantially 50 GPa or greater. In one embodiment magnetic nanoparticles are injected into a breast and the lymph nodes collecting the particles are detected with the probe and deemed sentinel nodes.

19 Claims, 4 Drawing Sheets

Related U.S. Application Data continuation of application No. 16/859,355, filed on Apr. 27, 2020, now Pat. No. 11,592,501, which is a continuation of application No. 12/631,370, filed on Dec. 4, 2009, now Pat. No. 10,634,741.

(51) Int. Cl.

| | |
|---|---|
| *A61B 5/06* | (2006.01) |
| *A61K 49/18* | (2006.01) |
| *B82Y 5/00* | (2011.01) |
| *G01R 33/12* | (2006.01) |
| *A61B 17/00* | (2006.01) |

(52) U.S. Cl.

CPC ............ *A61B 5/418* (2013.01); *A61B 5/4312* (2013.01); *A61K 49/1863* (2013.01); *B82Y 5/00* (2013.01); *A61B 2017/00876* (2013.01); *A61B 2562/12* (2013.01)

(56) References Cited

U.S. PATENT DOCUMENTS

| | | | |
|---|---|---|---|
| 3,449,662 | A | 6/1969 | Wood |
| 4,324,255 | A | 4/1982 | Barach et al. |
| 4,825,162 | A | 4/1989 | Roemer et al. |
| 4,983,912 | A | 1/1991 | Roehrlein et al. |
| 5,005,001 | A | 4/1991 | Cordery |
| 5,184,070 | A | 2/1993 | Besendorfer et al. |
| 5,261,403 | A | 11/1993 | Saito et al. |
| 5,293,119 | A | 3/1994 | Podney |
| 5,363,845 | A | 11/1994 | Chowdhury et al. |
| 5,402,094 | A | 3/1995 | Enge |
| 5,414,356 | A | 5/1995 | Yoshimura et al. |
| 5,416,413 | A | 5/1995 | Leussier |
| 5,437,280 | A | 8/1995 | Hussman |
| 5,512,821 | A | 4/1996 | Ando et al. |
| 5,534,778 | A | 7/1996 | Loos et al. |
| 5,537,037 | A | 7/1996 | Otaka et al. |
| 5,657,756 | A | 8/1997 | Vrba et al. |
| 5,666,052 | A | 9/1997 | Sata |
| 5,844,140 | A | 12/1998 | Seale |
| 5,942,209 | A | 8/1999 | Leavitt et al. |
| 5,997,473 | A | 12/1999 | Taniguchi et al. |
| 6,076,008 | A | 6/2000 | Bucholz |
| 6,082,366 | A | 7/2000 | Andrä et al. |
| 6,173,715 | B1 | 1/2001 | Sinanan et al. |
| 6,205,352 | B1 | 3/2001 | Carroll |
| 6,230,038 | B1 | 5/2001 | von Gutfeld et al. |
| 6,270,464 | B1 | 8/2001 | Fulton, III et al. |
| 6,304,075 | B1 | 10/2001 | von Schaewen et al. |
| 6,347,241 | B2 | 2/2002 | Burbank et al. |
| 6,356,782 | B1 | 3/2002 | Sirimanne et al. |
| 6,371,904 | B1 | 4/2002 | Sirimanne et al. |
| 6,394,965 | B1 | 5/2002 | Klein |
| 6,406,420 | B1 | 6/2002 | McCarthy et al. |
| 6,418,335 | B2 | 7/2002 | Avrin et al. |
| 6,427,081 | B1 | 7/2002 | Burbank et al. |
| 6,445,185 | B1 | 9/2002 | Damadian et al. |
| 6,549,800 | B1 | 4/2003 | Atalar et al. |
| 6,592,608 | B2 | 7/2003 | Fisher et al. |
| 6,603,308 | B2 | 8/2003 | Itozaki et al. |
| 6,638,913 | B1 | 10/2003 | Speck et al. |
| 6,662,040 | B1 | 12/2003 | Henrichs et al. |
| 6,662,041 | B2 | 12/2003 | Burbank et al. |
| 6,699,205 | B2 | 3/2004 | Fulton, III et al. |
| 6,725,083 | B1 | 4/2004 | Burbank et al. |
| 6,766,186 | B1 | 7/2004 | Hoyns et al. |
| 6,815,949 | B2 | 11/2004 | Kandori et al. |
| 6,835,572 | B1 | 12/2004 | Mountford et al. |
| 6,836,118 | B2 | 12/2004 | Molyneaux et al. |
| 6,850,065 | B1 | 2/2005 | Fujita et al. |
| 6,862,470 | B2 | 3/2005 | Burbank et al. |
| 6,889,073 | B2 | 5/2005 | Lampman et al. |
| 6,920,346 | B2 | 7/2005 | Kazandjian et al. |
| 6,949,926 | B2 | 9/2005 | Murakami et al. |
| 6,963,769 | B1 | 11/2005 | Balaban et al. |
| 6,996,433 | B2 | 2/2006 | Burbank et al. |
| 7,009,398 | B2 | 3/2006 | Hahn et al. |
| 7,044,957 | B2 | 5/2006 | Foerster et al. |
| 7,084,631 | B2 | 8/2006 | Qu et al. |
| 7,116,094 | B2 | 10/2006 | Levin et al. |
| 7,229,417 | B2 | 6/2007 | Foerster et al. |
| 7,283,868 | B2 | 10/2007 | Ko et al. |
| 7,329,414 | B2 | 2/2008 | Fisher et al. |
| 7,335,511 | B2 | 2/2008 | Mountford et al. |
| 7,386,338 | B2 | 6/2008 | Hoppel et al. |
| 7,412,275 | B2 | 8/2008 | Marinelli |
| 7,416,533 | B2 | 8/2008 | Gellman et al. |
| 7,479,784 | B2 | 1/2009 | Lee |
| 7,525,308 | B2 | 4/2009 | Tsukada et al. |
| 7,535,363 | B2 | 5/2009 | Gisselberg et al. |
| 7,570,056 | B2 | 8/2009 | Nakabayashi et al. |
| 7,625,397 | B2 | 12/2009 | Foerster et al. |
| 7,668,582 | B2 | 2/2010 | Sirimanne et al. |
| 7,676,256 | B2 | 3/2010 | Satragno et al. |
| 7,680,524 | B2 | 3/2010 | Ogawa et al. |
| 7,689,267 | B2 | 3/2010 | Prince |
| 7,701,209 | B1 | 4/2010 | Green |
| 7,702,378 | B2 | 4/2010 | Bolan et al. |
| 7,711,407 | B2 | 5/2010 | Hughes et al. |
| 7,744,852 | B2 | 6/2010 | Chernomorsky et al. |
| 7,783,336 | B2 | 8/2010 | Macfarlane et al. |
| 7,792,569 | B2 | 9/2010 | Burbank et al. |
| 7,877,133 | B2 | 1/2011 | Burbank et al. |
| 7,972,619 | B2 | 7/2011 | Fisher |
| 8,050,742 | B2 | 11/2011 | Weizman |
| 8,060,183 | B2 | 11/2011 | Leopold et al. |
| 8,062,215 | B2 | 11/2011 | Voegele et al. |
| 8,064,987 | B2 | 11/2011 | Carr, Jr. |
| 8,118,754 | B1 | 2/2012 | Flynn et al. |
| 8,137,320 | B2 | 3/2012 | Mark et al. |
| 8,174,259 | B2 | 5/2012 | Hattersley et al. |
| 8,219,182 | B2 | 7/2012 | Burbank et al. |
| 8,277,391 | B2 | 10/2012 | Foerster et al. |
| 8,280,486 | B2 | 10/2012 | Miller et al. |
| 2001/0011155 | A1 | 8/2001 | Rapoport |
| 2001/0049481 | A1 | 12/2001 | Fulton, III et al. |
| 2002/0019595 | A1 | 2/2002 | Osborne et al. |
| 2002/0035324 | A1 | 3/2002 | Sirimanne et al. |
| 2003/0016010 | A1 | 1/2003 | Kandori et al. |
| 2003/0141868 | A1 | 7/2003 | Bakharev |
| 2003/0216632 | A1 | 11/2003 | McClure et al. |
| 2004/0109823 | A1 | 6/2004 | Kaplan |
| 2004/0236213 | A1 | 11/2004 | Jones et al. |
| 2005/0033157 | A1 | 2/2005 | Klein et al. |
| 2006/0293581 | A1 | 12/2006 | Piewes |
| 2007/0093726 | A1 | 4/2007 | Leopold et al. |
| 2007/0242132 | A1* | 10/2007 | Homan .............. A61B 1/00075 348/65 |
| 2008/0074109 | A1 | 3/2008 | Tsukada et al. |
| 2008/0097199 | A1 | 4/2008 | Mullen |
| 2008/0161848 | A1 | 7/2008 | Fisher |
| 2008/0228164 | A1 | 9/2008 | Nicoson et al. |
| 2008/0294036 | A1 | 11/2008 | Hoi et al. |
| 2009/0164161 | A1 | 6/2009 | Hong et al. |
| 2009/0201016 | A1 | 8/2009 | Hattersley et al. |
| 2009/0216082 | A1* | 8/2009 | Rabinovitz ........ A61B 10/0045 600/118 |
| 2010/0030149 | A1 | 2/2010 | Carr, Jr. |
| 2010/0305430 | A1 | 12/2010 | Troesken |
| 2011/0021888 | A1 | 1/2011 | Sing et al. |
| 2011/0133730 | A1 | 6/2011 | Hattersley |
| 2011/0137154 | A1 | 6/2011 | Hattersley et al. |
| 2012/0229130 | A1 | 9/2012 | Hattersley et al. |

FOREIGN PATENT DOCUMENTS

| | | |
|---|---|---|
| EP | 0126580 | 11/1984 |
| EP | 0595227 | 5/1994 |
| EP | 0663599 | 5/1994 |
| EP | 0966924 | 5/1997 |
| EP | 1249207 | 10/2002 |
| EP | 1062911 | 8/2003 |
| EP | 1284123 | 7/2005 |

(56)  References Cited

FOREIGN PATENT DOCUMENTS

| EP | 1491147 | 3/2010 |
|---|---|---|
| EP | 2267471 | 12/2010 |
| EP | 2339343 | 6/2011 |
| FR | 2689638 | 10/1993 |
| FR | 2770779 | 5/1999 |
| GB | 2109112 | 5/1983 |
| GB | 2425610 | 1/2006 |
| JP | 02-078983 | 11/1990 |
| JP | 02-281170 | 11/1990 |
| JP | 05-251774 | 9/1993 |
| JP | 06-324021 | 11/1994 |
| JP | 08-015229 | 1/1996 |
| JP | 08-248004 | 9/1996 |
| JP | 08-338864 | 12/1996 |
| JP | 10-038854 | 2/1998 |
| JP | 2003-149212 | 5/2003 |
| JP | 2005-168678 | 6/2005 |
| JP | 2006-030004 | 2/2006 |
| JP | 09-027057 | 8/2014 |
| WO | 1995004287 | 2/1995 |
| WO | 9807052 | 2/1998 |
| WO | 2000038579 | 7/2000 |
| WO | 2002039917 | 5/2002 |
| WO | 2005011512 | 2/2005 |
| WO | 2006009048 | 1/2006 |
| WO | 2006056739 | 6/2006 |
| WO | 2006117530 | 11/2006 |
| WO | 2007034196 | 3/2007 |
| WO | 2007053533 | 5/2007 |
| WO | 2011033306 | 3/2011 |
| WO | 2011067576 | 6/2011 |
| WO | 2014013235 | 1/2014 |

OTHER PUBLICATIONS

Jakub et al., "Current Status of Radioactive Seed for Localization of Non Palpable Breast Lesions", The American Journal of Surgery, vol. 199, No. 4, Apr. 2010, pp. 522-528.

Meenach, "Synthesis and Characterization of Magnetic Hydrogel Nanocomposites for Cancer Therapy Applications", Dcotoral Dissertations, paper 108, 2010, http://uknowledge.uky.edu/gradschool_diss/108.

Postma et al., "Localization of Nonpalpable Breast Lesions", Expert Rev. Anticancer Ther., vol. 11, No. 8, 2011, pp. 1295-1302.

Reddy et al., "Preparation & Application of Magnetic Hydrogel Nanocomposites for Protein Purification and Metal Absorption", International conference on Advances in Polymer Technology, Feb. 26-27, 2010, India, pp. 83-97.

Freitas, Jr., "Nanomedicine, vol. I: Basic Capabilities", www. nanomedicine.com/NMI/8.2.1.2.htm, Landes Bioscience, Georgetown, TX, 1999, 4 pages.

PCT International Search Report and PCT Written Opinion of International Searching Authority for International Patent Application No. PCT/GB2013/051885, mailed Nov. 14, 2013, (18 pages).

European Search Report for EP 10180206, Nov. 23, 2010, 4 pages.

Material Safety Data Sheet; Revision Date Mar. 5, 2007; Retrieved from the Internet: URL:https://tools.lifetechnologies.com/content/sfs/msds/2007/11361D VIAL1_MTR-NAIV_EN.pdf [retrieved on Jun. 10, 2014]; abstract; (6 pages).

Harnan, S.E. et al.; "Magnetic resonance for assessment of axillary lymph node status in early breast cancer: A systematic review and meta-analysis"; EJSO the Journal of Cancer Surgery; 2011; vol. 37; pp. 928-936.

Tsay, Tzong T. et al.; "Deep Cervical Lymph Flow Following the Infusion of Mannitol in Rabbits"; Life Sciences; 1997; vol. 61; No. 19; pp. 1929-1934.

Williamson, S.J. et al.; "Biomagnetism"; Journal of Magnetism and Magnetic Materials; XP000574230; 1981; vol. 22; pp. 129-201.

Fagaly, "Squid Detection of Electronic Circuits", IEEE Transactions on Magnetics, vol. 25, No. 2, Mar. 1989, pp. 1216-1218.

Noguchi, et al., "Sentinel lymphadenectomy in breast cancer: identification of sentinel lymph node and detection of metastases," Breast Cancer Research and Treatment, vol. 53, 1999, pp. 97-104.

Kim, et al., "Near-infrared fluorescent type II quantum dots for sentinel lymph node mapping," Nat Biotechnol., vol. 22 (1), Jan. 2004, pp. 93-97.

Gopee, et al., "Migration of Intradermally Injected Quantum Dots to Sentinel Organs in Mice," Toxicological Sciences, vol. 98(1), Apr. 2007, pp. 249-257.

Soltesz, et al., "Intraoperative Sentinel Lymph Node Mapping of the Lung Using Near-Infrared Fluorescent Quantum Dots," Ann Thorac. Surg., vol. 79(1), Jan. 2005, pp. 269-277 (reproduced from NIH Public Access).

Peleg, et al., "Implementing metal detector technology and a navigation system in the removal of shrapnel," Computer Aided Surgery, Dec. 2009, vol. 14, No. 1-3; pp. 63-68.

Conners, "Diagnostic uses of metal detectors: a review," Int. J. Clin. Pract., Aug. 2005:59(8), pp. 946-949, Blackwell Publishing.

Cash, et al., "Breast Cancers: Noninvasive Method of Preoperative Localization with Three-dimensional US and Surface Contour Mapping," Published online before print Sep. 21, 2007, doi: 10.1148/radiol.2452060906; Nov. 2007, Radiology, 245, 556-566 (downloaded on Sep. 28, 2011 from http://radiology.rsna. org/content/245/2/556.full).

Peleg, et al., "Integration of computer-aided navigation and metal detector technology in the removal of shrapnel in terror attacks casualties," 7th Int. Conf. Computer-Aided Orthopaedic Surgery, Heidelberg, Germany, 2007 pp. 57-60.

Gunasekera, et al., "Imaging applications of nanotechnology in cancer," Targeted Oncology, 2009, vol. 4, pp. 169-181.

PCT International Search Report and Written Opinion of International Searching Authority for International Patent Application No. PCT/GB2010/002233, mailed Mar. 16, 2011, 15 pages.

* cited by examiner

MAGNETIC PROBE APPARATUS

CROSS-REFERENCE TO RELATED APPLICATIONS

This application is a continuation of U.S. patent application Ser. No. 18/103,828 filed on Jan. 31, 2023 which is a continuation of U.S. patent application Ser. No. 16/859,355 filed on Apr. 27, 2020, now U.S. Pat. No. 11,592,501, which is a continuation of Ser. No. 12/631,370, filed on Dec. 4, 2009, now U.S. Pat. No. 10,634,741, the disclosures of which are herein incorporated by reference in their entirety.

FIELD OF INVENTION

This invention relates to the field of medical diagnostic devices and more specifically to a device to detect tissues of interest during a surgical procedure.

BACKGROUND

Approximately 1.25 million new cases of breast cancer are diagnosed each year. In a majority of these cases, there is an urgent need for surgery to remove the tumor and to excise the sentinel lymph nodes and inspect them histologically to determine whether the cancer has spread to other sites in the body. The sentinel lymph nodes are the first nodes to receive lymphatic drainage from the tumor. They are called this because they reliably alert the clinician to any cancer spread. A sentinel lymph node biopsy is a standard of care in breast cancer operations today.

Locating sentinel nodes during surgery is difficult. One method for locating the sentinel node is to inject a dark blue dye into the lymphatic system in the breast. The dye then disperses throughout the breast lymphatic system and the surgeon removes any colored nodes. This method is recognized as being error-prone.

An improved method involves injecting a radioactive dye into the lymph nodes. In a similar manner, the dye drains through the lymphatic system and the surgeon then uses a radiation detector to help locate the sentinel nodes. However, the use of radioisotopes presents a significant, and an expensive, logistical burden, because of the need to allocate the time and resources of a nuclear medicine radiologist in addition to the surgeon for what is otherwise a routine operation. Further many patients are reluctant to receive a radioactive injection. These factors become a significant barrier to the widespread adoption of the use of radioisotopes to locate the sentinel nodes.

The present invention overcomes these issues.

SUMMARY OF THE INVENTION

The present invention radically alters the sentinel lymph node protocol through the use of a detection system based on magnetism rather than radiation. The present system combines the magnetic properties of a magnetic nanoparticle suspension with a detector that is significantly more sensitive than other methods that can be used in the environment of an operating theater. In one embodiment the nanoparticles suspension is an FDA approved MRI contrast agent. Although in one embodiment the present invention is directed to locating sentinel lymph nodes, it can be used to detect other magnetic materials both within a body and in other environments.

In one aspect the invention relates to a system for locating magnetic material. In one embodiment the system includes a magnetic probe; a power module in electrical communication with the magnetic probe to supply current to the magnetic probe; a sense module in electrical communication with the magnetic probe to receive signals from the magnetic probe; and a computer in electrical communication with the power module and the sense module. The computer generates a waveform that controls the supply of current from the power module and receives a signal from the sense module that indicates the position of magnetic material. The magnetic probe is constructed from a material having a coefficient of thermal expansion of substantially $10^{-6}/^\circ$ C. or less and a Young's modulus of substantially 50 GPa or more.

In one embodiment the magnetic probe comprises two concentric drive coils positioned on respective sides of a concentric sense coil. The two concentric drive coils are constructed so as to produce a zero magnetic field at the center of the sense coil. In another embodiment the magnetic probe further comprises an optional sense coil positioned away from the drive coils and constructed so as to cancel the ambient magnetic field effects in the sense coil. In yet another embodiment the probe is cylindrical and the drive and sense coils are positioned within respective circumferential grooves in the cylindrical magnetic probe. In still yet another embodiment an additional circumferential groove is constructed in the cylinder to reduce heat conduction.

In another embodiment the magnetic probe comprises two concentric sense coils positioned on respective sides of a concentric drive coil. The two concentric sense coils are constructed so as to produce equal and opposite currents in response to the magnetic field generated by the drive coil.

In another aspect the invention relates to a magnetic probe comprising a probe body having a first end and a second end. The probe body is sized to fit in the hand of a user and comprises a material having a coefficient of thermal expansion less than or equal to $10^{-6}/^\circ$ C. and a Young's modulus of substantially 50 GPa or greater. A sense coil is positioned near the first end of the probe body, and two concentric drive coils are positioned concentric with and on respective sides of the sense coil. The two concentric drive coils are constructed so as to produce a zero magnetic field at the center of the sense coil. In one embodiment the magnetic probe further comprises an optional sense coil positioned away from the drive coils and constructed so as to cancel ambient field effects in the sense coil. In another embodiment the probe is cylindrical and the drive and sense coils are positioned within respective circumferential grooves in the cylindrical magnetic probe. In yet another embodiment an additional circumferential groove is constructed in the cylinder to reduce heat conduction.

In yet another aspect, the invention relates to a magnetic probe comprising a probe body having a first end and a second end. The probe body is sized to fit in the hand of a user and comprises a material having a coefficient of thermal expansion less than or equal to $10^{-6}/^\circ$ C. and a Young's modulus of substantially 50 GPa or greater. A drive coil is positioned near the first end of the probe body and two concentric sense coils are positioned concentric with and on respective sides of the drive coil. The two concentric sense coils are constructed so as to produce equal and opposite currents in response to the magnetic field generated by the drive coil.

In one embodiment the magnetic probe further comprises an optional sense coil positioned away from the drive coils and constructed so as to cancel ambient magnetic field effects in the sense coil. In another embodiment the probe is cylindrical and the drive and sense coils are positioned within respective circumferential grooves in the cylindrical magnetic probe. In yet another embodiment an additional circumferential groove is constructed in the cylinder to reduce heat conduction.

Still yet another aspect of the invention relates to a system for detecting sentinel nodes in a breast lymph system. In one embodiment the apparatus comprises a magnetic probe; a power module in electrical communication with the magnetic probe to supply current to the magnetic probe; a sense module in electrical communication with the magnetic probe to receive signals from the magnetic probe; and a computer in electrical communication with the power module and the sense module. The computer generates a waveform that controls the supply of current from the power module to the magnetic probe and receives a signal from the sense module that indicates the position of a magnetic particle in the lymph system. The magnetic probe is constructed from a material having a coefficient of thermal expansion less than or equal to $10^{-6}/°$ C. and a Young's modulus of substantially 50 GPa or greater.

In one embodiment the magnetic probe comprises two concentric drive coils positioned on respective sides of a concentric sense coil. The two concentric drive coils are constructed so as to produce a zero magnetic field at the center of the sense coil. In another embodiment the magnetic probe further comprises an optional sense coil positioned away from the drive coils and constructed so as to cancel ambient magnetic field effects in the sense coil. In yet another embodiment the probe is cylindrical and the drive and sense coils are positioned within respective circumferential grooves in the cylindrical magnetic probe. In still yet another embodiment an additional circumferential groove is constructed in the cylinder to reduce heat conduction. In another embodiment the magnetic probe comprises two concentric sense coils positioned on respective sides of a concentric drive coil and wherein the two concentric sense coils are constructed so as to produce equal and opposite currents in response to the magnetic field generated by the drive coil.

In another aspect the invention relates to a magnetic probe including a pair of drive coils and a sense coil. The pair of drive coils and sense coil have different radii. The spacing between the drive coils and the sense coil is such that the rate of change of their mutual inductance with respect to the radius of the larger coil is substantially zero.

In another aspect the invention relates to a magnetic probe magnetic probe having a pair of sense coils, and a drive coil. The pair of sense coils and drive coil have different radii. The spacing between the drive coil and the sense coils is such that the rate of change of their mutual inductance with respect to the radius of the larger coil is substantially zero.

In yet another aspect the invention relates to a method for constructing magnetic probe. The method includes the steps of providing a pair of first coils, and providing a second coil, the pair of first coils and the second coil having different radii, and placing the pair of first coils and the second coil in the probe such that the spacing between the first coils and the second coil is such that the rate of change of their mutual inductance with respect to the radius of the larger coil is substantially zero.

In another aspect the invention relates to a method for detecting sentinel nodes in a breast lymphatic system. In one embodiment the method comprises the steps of: injecting a suspension of magnetic nanoparticles into the tissue of the breast; and scanning the axillary lymph nodes in the armpit, on the same side as the breast, with a magnetic probe. The magnetic probe includes a probe body having a first end and a second end. The probe body is sized to fit in the hand of a user and includes a material having a coefficient of thermal expansion less than or equal to $10^{-6}/°$ C. and a Young's modulus of substantially 50 GPa or more. A sense coil is positioned near the first end of the probe body and two concentric drive coils positioned concentric with and on respective sides of the sense coil. The two concentric drive coils are constructed so as to produce a zero magnetic field at the center of the sense coil. In one embodiment the magnetic injection is a suspension of magnetic particles. In another embodiment the type of magnetic nanoparticle is a ferum oxide.

BRIEF DESCRIPTION OF THE DRAWINGS

The objects and features of the invention can be better understood with reference to the drawings described below. The drawings are not necessarily drawn to scale; emphasis is instead being placed on illustrating the principles of the invention. In the drawings, numerals are used to indicate specific parts throughout the various views. The drawings associated with the disclosure are addressed on an individual basis within the disclosure as they are introduced.

DETAILED DESCRIPTION

The following description refers to the accompanying drawings that illustrate certain embodiments of the invention. Other embodiments are possible and modifications may be made to the embodiments without departing from the spirit and scope of the invention. Therefore, the following detailed description is not meant to limit the invention. Rather, the scope of the invention is defined by the appended claims.

Figure 1:
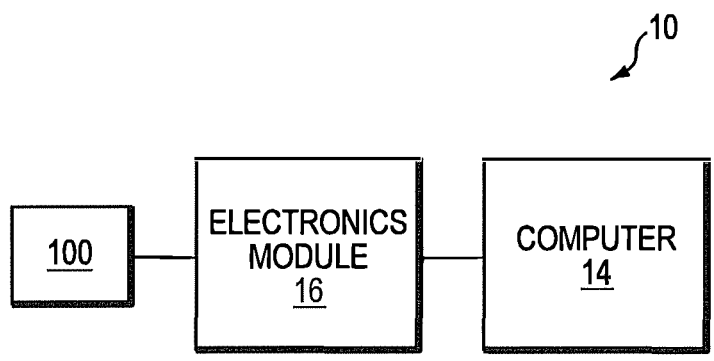
FIG. 1 is a block diagram of an embodiment of a system constructed in accordance with the invention.

Referring to FIG. 1, in brief overview, a system 10 constructed in accordance with the teachings of the invention includes a computer 14 having a processor, RAM memory, long term data storage, input/output devices and display; an electronic module 16 containing the power and sensor electronics for the probe and the probe itself 100. In one embodiment the input/output devices include a digital to analog converter and an analog to digital converter.

Figure 2:
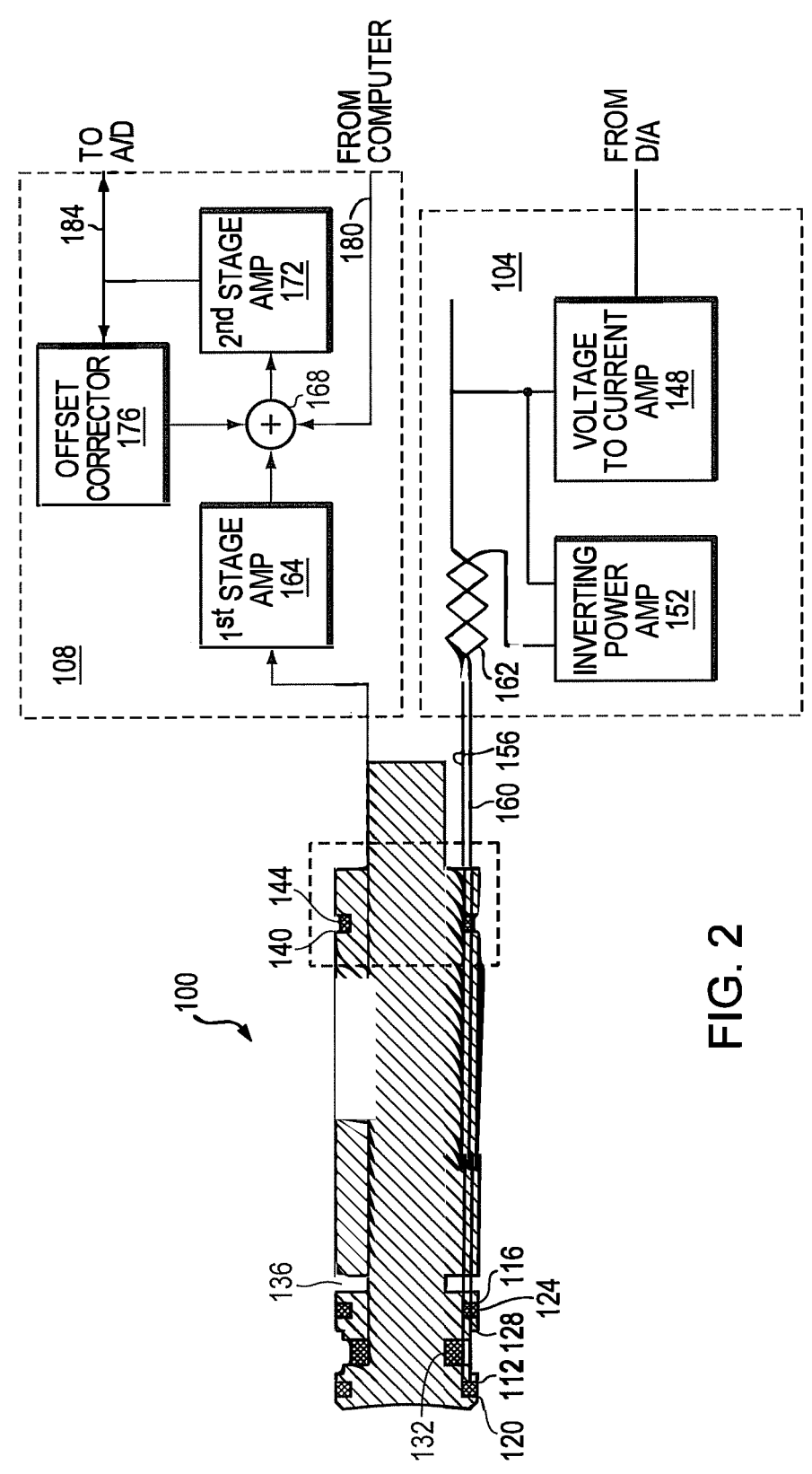
FIG. 2 is a schematic diagram of the probe and electronic components of the embodiment of the system of the system shown in FIG. 1.

To maintain the stability of the system, it is necessary in part to provide thermal stability in the probe. This is done with a combination of a material having a combination of low thermal expansion and a high resistance to deformation with a careful positioning of the coils of the probe. Referring to FIG. 2, an embodiment of the electronics and probe components of the system of the invention includes the probe 100, a drive circuit 104 and a sense circuit 108. The probe 100 is generally a cylindrically shaped device sized to fit the hand of a user. In one embodiment the cylinder is about 75 mm long and 20 mm in diameter. In one embodiment the cylinder is made of Zerodur®, (Schott AG, Mainz, Germany) which is an inorganic, non-porous glass ceramic that has a non-directional, isotropic structure. During formation, this glass ceramic is subjected to thermal cycling which converts about 75% of the vitreous material into crystalline quartz. The resulting glass and crystal phases within the material balance such that the thermal expansion coefficient of one form of Zerodur® is of the order $0.02 \times 10^{-6}/°$ C. The substantially zero coefficient of expansion maintains the mechanical stability of the probe 100 over a wide temperature range. In addition the glass ceramic material is very stiff having a Young's modulus of 90 GPa. Other materials with coefficients of thermal expansion and Young's modulus similar to this material may also be used.

In one embodiment two grooves 112 and 116 are circumferentially formed near the first end of the cylinder body and two substantially identically sized coils of wire 120, 124 are wound in the grooves. A third groove 128 is also formed in the cylinder substantially midway between and coaxial with the first 112 and second 116 grooves and a third coil 132 wound in that groove 128.

In this embodiment the depth of the third groove 128 is such that the outer surface of the third coil 132 is located at the same depth as the bottom of the first 112 and second 116 grooves and the groove 128 is wider than the other two grooves. In one embodiment the first 120 and second 124 coils are about 2 mm wide; have an inner radius of about 8 mm; and have about 48 turns of wire. The third coil 132 is about 3 mm wide; has an inner radius of about 5 mm and contains about 72 turns of wire.

The size of the coils and their placement relative to each other is selected so that as the coils change shape because of heating, their inductive change is minimized. Unfortunately there are presently no available electrical conductors with zero coefficient of thermal expansion. Tungsten wire offers an improvement over copper wire, reducing the coefficient by a factor of four, but it also suffers from four times the resistivity. For the drive coils the higher resistivity causes increased self-heating, for sense coils the increased resistivity increases the noise, so in the embodiments shown tungsten was not used.

The problem of differential radial expansion of the coils cannot be addressed through material selection, but it can be handled by careful calculation of coil geometry. Consider the coupling (mutual inductance) between a pair of coaxial coils, one of which has a larger radius than the other. If the coils are close together, then the coupling is reduced as the larger coil expands. If the coils are far apart, the coupling increases as the larger coil expands. Thus it is evident that there is a separation at which the coupling is unaffected by small expansions of the larger coil.

With real coils of non-zero radius, length and thickness, the mutual inductance can be calculated numerically as an integral of order 6 over the two coil volumes. Assuming the radii are selected first, the required separation may be determined iteratively. The mutual inductance between two filamentary circuits i and j is given by the Neumann formula:

$$M_{ij} = \frac{\mu}{4\pi} \oint_{c_i} \oint_{c_j} \frac{ds_i \cdot ds_j}{|R_{ij}|}$$

where $R_{ij}$ is the distance between elements $ds_i$ and $ds_j$ on circuits $C_i$ and $C_j$. and $\mu$ is the magnetic permeability of the material between the filamentary circuits, which for glass ceramics is typically very close to $\mu_0$, the permeability of free space.

For volume-filling coaxial cylindrical coils, this equation becomes (in cylindrical polar coordinates (r, θ, z):

$$M_{ij} = \frac{\mu}{4\pi} N_i N_j \int_{r_{j_0}}^{r_{j_1}} \int_{r_{i_0}}^{r_{i_1}} \int_{z_{j_0}}^{z_{j_1}} \int_{z_{i_0}}^{z_{i_1}} \int_{-\pi}^{\pi} \int_{-\pi}^{\pi} \frac{\cos(\theta_i - \theta_j)}{|R_{ij}|}$$

$$r_i d\theta_i r_j d\theta_j \frac{dz_i}{z_{i_1} - z_{i_0}} \frac{dz_j}{z_{j_1} - z_{j_0}} \frac{dr_i}{r_{i_1} - r_{i_0}} \frac{dr_j}{r_{j_1} - r_{j_0}}$$

where $$|R_{ij}|^2 = r_i^2 + r_j^2 - 2r_i r_j \cos(\theta_i - \theta_j) + (z_i - z_j)^2$$

and where Ni, Nj are the number of turns on each coil. This equation assumes a uniform current distribution over the coil cross-section, which is valid for low frequency and small wire size so that the skin effect can be neglected.

Given axial symmetry, one integral reduces to the circumference of a circle, leaving the following formula to be integrated numerically:

$$M_{ij} = \mu N_i N_j \int_{r_{j_0}}^{r_{j_1}} \int_{r_{i_0}}^{r_{i_1}} \int_{z_{j_0}}^{z_{j_1}} \int_{z_{i_0}}^{z_{i_1}} r_i r_j$$

$$\int_0^\pi \frac{\cos(\theta_j) d\theta_j}{\sqrt{r_i^2 + r_j^2 - 2r_i r_j \cos(\theta_j) + (z_i - z_j)^2}} \frac{dz_i}{z_{i_1} - z_{i_0}} \frac{dz_j}{z_{j_1} - z_{j_0}} \frac{dr_i}{r_{i_1} - r_{i_0}} \frac{dr_j}{r_{j_1} - r_{j_0}}$$

It should be understood that the coil coupling is only insensitive to variation in the size of the larger coil, not to variation in the size of the smaller coil. For this technique to be effective, it is therefore necessary that the smaller coil is the central coil within a first order gradiometer made from two equal larger coils. Any change in the radius of the centre coil is balanced by an equal change in coupling to the coils on either side of it. A change in radius of either larger coil is compensated by its correct positioning.

A fourth groove 136 is also formed in the cylinder to reduce the thermal conductivity of the cylinder in use and reduce the amount of any heat generated by the coils 120, 124 from flowing along the cylinder causing a thermal asymmetry and thereby making the local environment of the two coils 120, 124 different. Two longitudinal grooves (not shown) are also formed in the surface along the length of the cylinder to provide paths for the wire connections to the various coils.

An optional fifth groove 140 may be formed near the end of the cylinder away from the first groove 112, and an optional fourth coil 144 formed in the groove 140. In one embodiment, the fourth coil 144 is about 2 mm wide; has an inner radius of 8 mm and has about 32 turns of wire. Although the fourth coil 144 is larger than the third coil 132, their area-turns are substantially matched.

In one embodiment the first 120 and second 124 coils are counter wound and connected in series such that when energized by a current, the magnetic fields they produce are substantially cancelled at the center of the third coil 132. For the purposes of this discussion, unless otherwise stated, the first 120 and second 124 coils are referred to as the drive coils and the third coil 132 as the sense coil. Also the fourth optional coil 144 will also be referred to as an optional sense coil.

Power is supplied to the drive coils 120, 124 by the drive circuit 104. The drive circuit includes a voltage to current amplifier 148 and an inverting power amplifier 152. In one embodiment the computer 14 generates a sine wave of appropriate amplitude and frequency and the digital to analog converter within the computer generates an analog voltage from this generated sine wave. In one embodiment the frequency of the sine wave is 10 kHz. The voltage to current amplifier 148 converts that voltage to a current used to power the drive coils 120, 124 through one series connected conductor 156. In one embodiment the current is 100 mA. The current return conductor 160 is connected to the output terminal of the inverting power amplifier whose input terminal is also connected to the output of the voltage to current amplifier 148. This configuration produces a balanced +V on one side of the drive coils 120, 124 and −V on the other side of the drive coils 120, 124.

The sense circuit 108 includes a first stage amplifier 164, a summing junction 168, a second stage amplifier 172, and an offset correction circuit 176. A signal received from the sense coil 132 is the input signal to the first stage sense amplifier 164. In one embodiment this amplifier has a gain of 250. The output of the first stage gain amplifier 164 is one input to the summing junction 168. The output of the summing junction 168 is the input to the second stage amplifier 172. In one embodiment the second stage amplifier has a gain of 400. The output of the second stage amplifier 172 is the input to the offset correction circuit 176 and the input to the analog to digital converter (not shown) connected to the computer 14.

The offset correction circuit 176 integrates the output of the second stage amplifier 172 and its output is a second input to the summing junction 168. The output of the offset correction circuit 176 provides a feedback signal in response to a positive offset to generate a negative ramp signal.

The third input to the summing junction 168 is a software controlled balance signal 180. This signal, which is generated by a second digital to analog converter (not shown) of the computer 10, is the signal which compensates for any unbalance in the sense coils 120, 124. To perform this compensation function the probe 100 is held pointing to open space. The computer 10 generates a compensating balance signal 180 and measures the change of amplitude and phase of the output signal 184. The computer 10 then calculates the vector (amplitude and phase) for the balance signal 180 necessary to null the output signal 184.

Thus the balancing process determines the balance phasor required to obtain a near-zero output from the system. Normally balancing starts with the existing value. When starting without a prior value it may be necessary to use a lower drive current initially to avoid saturating the input, and then repeat the balancing at the required drive current.

The system measures the response $S_0$ at the original balance setting $B_0$, then adjusts the balance phasor by a small amount to $B_1$ and measures the new response $S_1$. The coupling from the balance output to the detected input is defined by:

$$X = \frac{S_1 - S_0}{B_1 - B_0}$$

which is the rate of change of the response to balance and therefore the new balance is reached when:

$$B_2 = B_0 - \frac{S_0}{X}$$

Alternatively the computer 10 can generate a balance signal 180, measure the output signal 184 and modify the balance signal 180 iteratively until the output signal 184 is nulled.

To reduce the noise in the system, the optional sense coil 144 is utilized. This coil 144 is positioned away from the drive coils 120, 124 and generally detects the magnetic flux in the operating room and not the magnetic flux from the drive coils 120. This optional coil 144 can be connected in series with the sense coil 132 such that any ambient magnetic field will produce a current in the optional sense coil 144 that is in opposition to the current that is produced by the ambient magnetic field on the sense coil 132, thereby canceling the effects of the ambient magnetic field on the probe 100. It should be noted that when coils are configured to cancel the effects of other coils, the coils canceling each other may be counter wound, or connected in series with their input and output leads reversed.

Further, the functions of the drive coils 120, 124 and the sense coil 132 can be reversed. If this is done this forms an embodiment in which there are two sense coils 120, 124 connected in opposition and a drive coil 132 positioned between them. The sense coils 120, 124 are constructed such that the field of from the drive coil 132 produces a current in each of the sense coils 120, 124 that is equal and opposite to the current produced in the other sense coil 124, 120. The optional sense coil 144 is not needed in this configuration.

To reduce the noise in the system, the power to the coils 120, 124 and the signals from the sense coil 132 to the sense electronics 108 are each conducted by a twisted quad microphone cable for improved magnetic field rejection. Further the two twisted quad cables are both embedded in a longitudinally flexible yet laterally stiff sheath which prevents the conductors from moving relative to one another.

The output signal 184 from the sense circuit 108 is digitized by the computer's 14 analog to digital converter to provide an output time series. This time series is correlated to the output series generated by the computer 14.

In particular, detection of the magnetic particles involves correlating the sampled input waveform with two sinusoidal reference waveforms, one in phase with the drive and one in quadrature. The result is a phasor; a complex number giving the amplitude and phase of the probe response:

$$S = \frac{2\sum_N C_i V_i}{N} + i\frac{2\sum_N S_i V_i}{N}$$

where $V_i$ is the sampled input voltage and $C_i$ and $S_i$ are sampled cosine and sine waves respectively, and the input is processed in sections of N samples.

It is possible to use the amplitude |S| as the system indication, in which case both magnetic and conductive materials are detected, or to use the dot product with a discrimination phasor to detect only the magnetic component. This works because the eddy current induced in a conductive material is in quadrature with the applied field, while the magnetization of a magnetic material at low frequency is in phase with the applied field. Thus the system can be used not only for detecting magnetic materials but also conductive materials.

As the probe 100 is positioned closer to a node with magnetic particles, the results are displayed, in one embodiment, as an audible sound of increasing frequency and a graphics display of counts proportional to the detected field.

Figure 4:
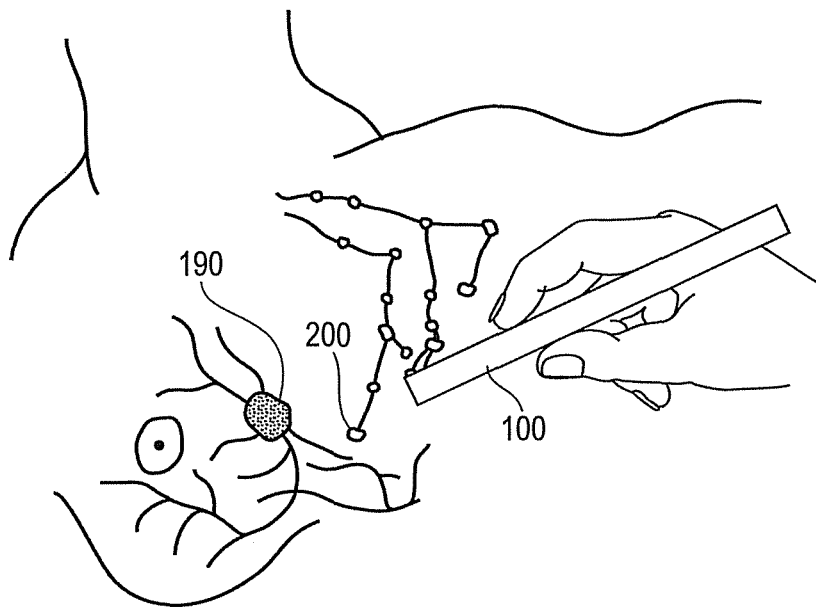
FIG. 4 is a drawing of the probe of the system being used to locate a sentinel node.
Figure 3:
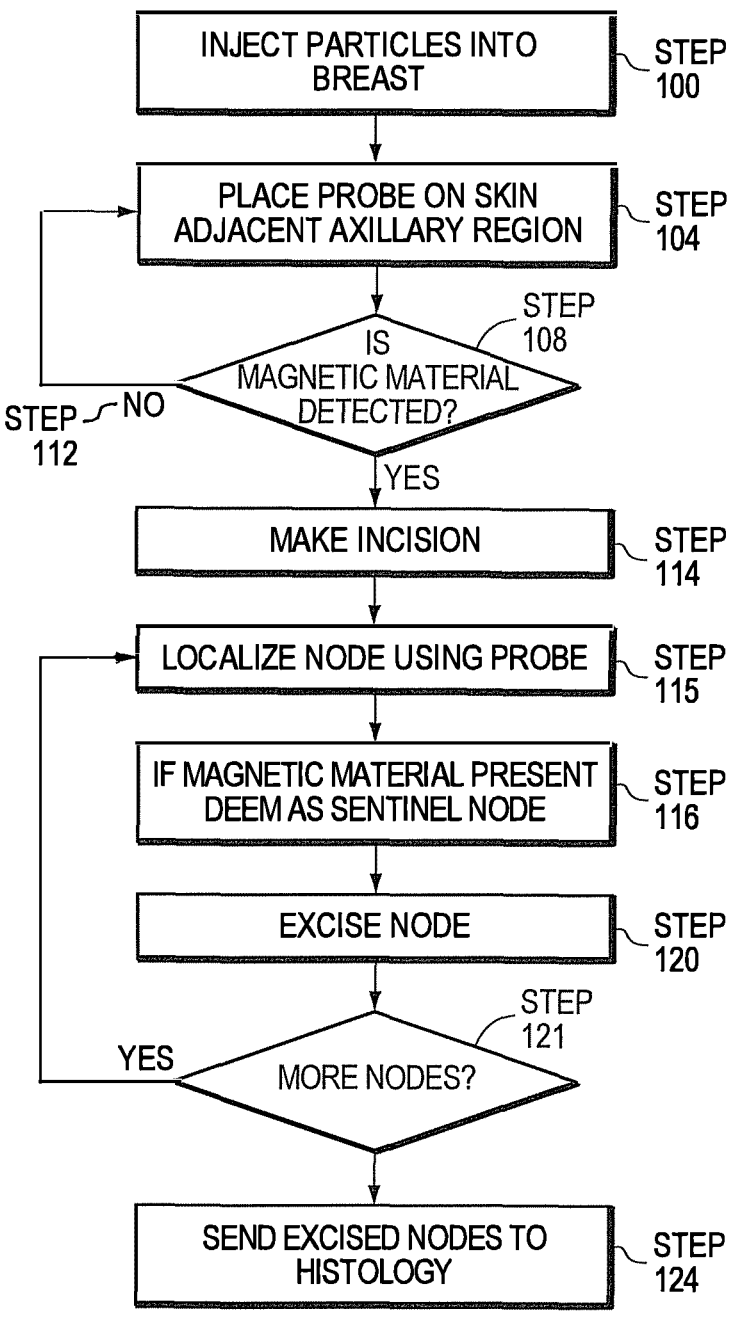
FIG. 3 is a flow diagram of an embodiment the method of determining the sentinel nodes utilizing the invention.

Referring to FIG. 3, during a surgical operation, a surgeon injects (Step 100) the breast with a suspension of magnetic nanoparticles near a tumor 190 (FIG. 4). In one embodiment the nanoparticles are those used as an MRI contrast agent. Feridex® (Bayer HealthCare Pharmaceuticals, Montville, New Jersey) or Endorem™ (Guerbet, Paris, France) are ferum oxides used generally as an MRI contrast agent which are suitable for the magnetic detection purpose.

After a period of time the suspension drains into the axillary lymphatic system on the same side as the breast. The surgeon then places (Step 104, FIG. 3) the probe 100 on the surface of the skin, attempting to localize a lymph node 200 (FIG. 4) by determining if magnetic particles are detected (Step 108). If not (Step 112) the surgeon continues to search for a node by placing the probe 100 in another location on the surface of the skin and the process repeats. If a magnetic region is detected, the surgeon then makes an incision (Step 114) and attempts to localize the node with magnetic particles using the probe (Step 115). If the node has accumulated the magnetic nanoparticles, it is deemed (Step 116) a sentinel node. The node is then excised (Step 120). The surgeon then looks for additional nodes (Step 121) which may also be sentinel nodes and when complete sends the excised nodes for histological examination for evidence of cancer (Step 124).

Figure 5:
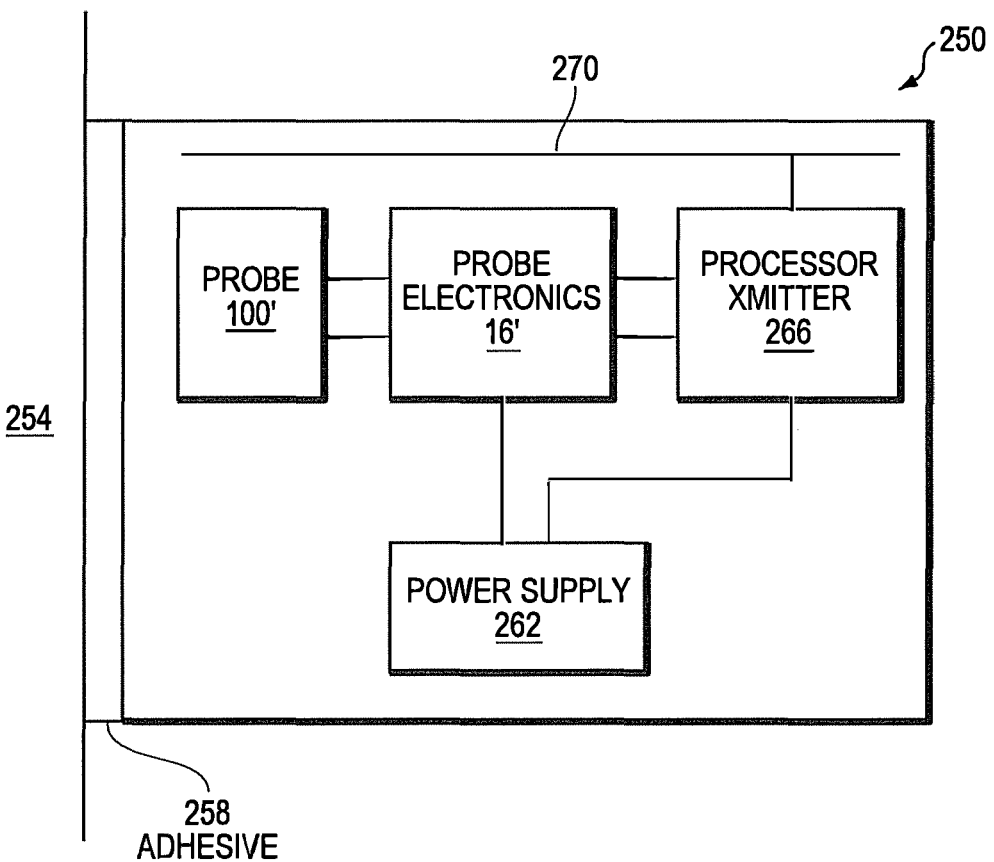
FIG. 5 is a block diagram of another embodiment of the system constructed for wireless use.

Referring to FIG. 5, the system of the invention may be used to study the long term properties of magnetic materials either in a biological context or otherwise. In one embodiment the probe 100' of the invention is reduced in size and rather than being held by a user is placed in a small capsule 250 that is attached to the object of interest 254 by an adhesive 258. The capsule 250 also houses a power supply battery 262, the probe electronics 16', a microprocessor and transmitter 266 and an antenna 270. The output of the probe electronics 16' is digitized by the microprocessor 266 and the data transmitted using the antenna 270 to a receiving computer system (not shown). This embodiment for example is useful in tracking the behavior of magnetic particles without requiring that the patient or object be tethered to the computer system 14 by wires.

It is to be understood that the figures and descriptions of the invention have been simplified to illustrate elements that are relevant for a clear understanding of the invention, while eliminating, for purposes of clarity, other elements. Those of ordinary skill in the art will recognize, however, that these and other elements may be desirable. However, because such elements are well known in the art, and because they do not facilitate a better understanding of the invention, a discussion of such elements is not provided herein. It should be appreciated that the figures are presented for illustrative purposes and not as construction drawings. Omitted details and modifications or alternative embodiments are within the purview of persons of ordinary skill in the art.

It can be appreciated that, in certain aspects of the invention, a single component may be replaced by multiple components, and multiple components may be replaced by a single component, to provide an element or structure or to perform a given function or functions. Except where such substitution would not be operative to practice certain embodiments of the invention, such substitution is considered within the scope of the invention.

The examples presented herein are intended to illustrate potential and specific implementations of the invention. It can be appreciated that the examples are intended primarily for purposes of illustration of the invention for those skilled in the art. There may be variations to these diagrams or the operations described herein without departing from the spirit of the invention. For instance, in certain cases, method steps or operations may be performed or executed in differing order, or operations may be added, deleted or modified.

Furthermore, whereas particular embodiments of the invention have been described herein for the purpose of illustrating the invention and not for the purpose of limiting the same, it will be appreciated by those of ordinary skill in the art that numerous variations of the details, materials and arrangement of elements, steps, structures, and/or parts may be made within the principle and scope of the invention without departing from the invention as described in the claims.

Variations, modification, and other implementations of what is described herein will occur to those of ordinary skill in the art without departing from the spirit and scope of the invention as claimed. Accordingly, the invention is to be defined not by the preceding illustrative description, but instead by the spirit and scope of the following claims.

What is claimed is:

1. A magnetic materials tracker comprising:
a capsule;
a probe disposed in the capsule;
an adhesive, the adhesive disposed on the capsule and configured to attach the capsule to an object of interest;
a power supply battery disposed in the capsule, the power supply battery in electrical communication with the probe;
a microprocessor disposed in the capsule, the microprocessor in electrical communication with the probe; and
an antenna disposed in the capsule, the antenna in electrical communication with the microprocessor;
wherein the probe is configured to generate an output in response to magnetic particles being detected by the probe, the magnetic particles disposed outside the capsule;
wherein the microprocessor is configured to digitize the output from the probe;
wherein the antenna is configured to transmit data from the microprocessor.

2. The magnetic materials tracker of claim 1, wherein the probe comprises
a drive coil having a first radius producing an alternating magnetic field, the drive coil configured to generate an alternating magnetic field, and
a sense coil having a second radius, the sense coil configured to detect a magnetic field generated by the magnetic particles in response to the alternating magnetic field generated by the drive coil.

3. The magnetic materials tracker of claim 2, wherein an axial spacing between the drive coil and the sense coil is such that while the first radius of the drive coil and the second radius of the sense coil expand in response to heating change in mutual inductance between the sense coil and the drive coil is inherently zero.

4. The magnetic materials tracker of claim 3, wherein the probe is cylindrical shaped, wherein the cylindrical shape defines an axis of the probe.

5. The magnetic materials tracker of claim 4, wherein the sense coil and the drive coil are disposed along the axis of the probe.

6. The magnetic materials tracker of claim 5, wherein the second radius is smaller than the first radius.

7. The magnetic materials tracker of claim 5, wherein the second radius is greater than the first radius.

8. The magnetic materials tracker of claim 3 further comprising probe electronics disposed in the capsule, the probe electronics in electrical communication with the probe.

9. The magnetic materials tracker of claim 3, wherein the magnetic particles are magnetic nanoparticles.

10. The magnetic materials tracker of claim 2, wherein the magnetic particles are deposited from Magnetic Resonance Imaging (MRI) contrast solution.

11. The magnetic materials tracker of claim 8, wherein the magnetic particles comprise a ferum oxide.

12. The magnetic materials tracker of claim 1, wherein the microprocessor is configured to generate a waveform that controls a supply of current from the power supply battery to the probe.

13. A magnetic materials tracker comprising:
a capsule comprising
a probe,
a power supply battery,
a microprocessor, and
an antenna,
an adhesive, the adhesive disposed on the capsule and configured to attached the capsule to skin surface of a patient;
wherein the probe is configured to generate an output in response to magnetic particles being detected by the probe, the magnetic particles disposed outside of the capsule;
where in the microprocessor is configured to digitize the output from the probe;

wherein the antenna is configured to transmit data from the microprocessor-;
wherein the probe comprises
a drive coil having a first radius producing an alternating magnetic field, the drive coil configured to generate an alternating magnetic field, and
a sensor coil having a second radius, the sense coil configured to detect a magnetic field generated by the magnetic particles in response to the alternating magnetic field generated by the drive coil.

14. The magnetic materials tracker of claim 13, wherein an axial spacing between the drive coil and the sense coil is such that while the first radius of the drive coil and the second radius of the sense coil expand in response to heating change in mutual inductance between the sense coil and the first drive coil is inherently zero.

15. The magnetic materials tracker of claim 14, wherein the probe is cylindrical shaped, wherein the cylindrical shape defines an axis of the probe.

16. The magnetic materials tracker of claim 15, wherein the sense coil and the drive coil are disposed along the axis of the probe.

17. The magnetic materials tracker of claim 16, wherein the second radius is smaller than the first radius.

18. The magnetic materials tracker of claim 16, wherein the second radius is greater than the first radius.

19. The magnetic materials tracker of claim 13, wherein the magnetic particles are magnetic nanoparticles.

\* \* \* \* \*